(12) United States Patent
You et al.

(10) Patent No.: US 12,270,762 B2
(45) Date of Patent: Apr. 8, 2025

(54) RAMAN-ACTIVE PARTICLE FOR SURFACE-ENHANCED RAMAN SCATTERING AND METHOD OF PRODUCING THE SAME

(71) Applicant: KOREA RESEARCH INSTITUTE OF STANDARDS AND SCIENCE, Daejeon (KR)

(72) Inventors: Eun-Ah You, Daejeon (KR); Wansun Kim, Daejeon (KR); Tae Geol Lee, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 953 days.

(21) Appl. No.: 16/982,850

(22) PCT Filed: Sep. 18, 2019

(86) PCT No.: PCT/KR2019/012072
§ 371 (c)(1),
(2) Date: Sep. 21, 2020

(87) PCT Pub. No.: WO2021/045287
PCT Pub. Date: Mar. 11, 2021

(65) Prior Publication Data
US 2023/0103705 A1  Apr. 6, 2023

(30) Foreign Application Priority Data
Sep. 5, 2019  (KR) ........................ 10-2019-0110212

(51) Int. Cl.
*G01N 21/65* (2006.01)
*B82B 1/00* (2006.01)
(Continued)

(52) U.S. Cl.
CPC ............... *G01N 21/65* (2013.01); *B82B 1/00* (2013.01); *B82Y 30/00* (2013.01); *B82Y 40/00* (2013.01);
(Continued)

(58) Field of Classification Search
CPC .... G01N 21/65; G01N 33/483; G01N 33/553; G01N 33/54346; B82B 1/00; B82Y 30/00
See application file for complete search history.

(56) References Cited

U.S. PATENT DOCUMENTS 6,514,767 B1 * 2/2003 Natan .................. G01N 21/658
436/166
2004/0219545 A1 * 11/2004 Rando .................. C10M 107/06
435/6.12
(Continued)

FOREIGN PATENT DOCUMENTS

| KR | 10-2011-0066881 A | 6/2011 |
| KR | 10-2014-0101980 A | 8/2014 |
| KR | 10-1986531 B1 | 6/2019 |

OTHER PUBLICATIONS

Li, M., Qiu, Y., Fan, C., Cui, K., Zhang, Y. and Xiao, Z., 2018. Design of SERS nanoprobes for Raman imaging: materials, critical factors and architectures. Acta pharmaceutica sinica B, 8(3), pp. 381-389. (Year: 2018).*
(Continued)

*Primary Examiner* — Uzma Alam
*Assistant Examiner* — Mohamed Doumbia
(74) *Attorney, Agent, or Firm* — Knobbe, Martens, Olson & Bear, LLP

(57) ABSTRACT

Provided is a Raman-active particle which is a Raman-active particle for surface-enhanced Raman analysis, the particle including: a spherical plasmonic metal core; a plasmonic metal shell having surface unevenness; and a self-assembled
(Continued)

monolayer which is bonded to each of the core and the shell and positioned between the core and the shell, and includes a Raman reporter.

17 Claims, 4 Drawing Sheets

(51) Int. Cl.
  *B82Y 30/00* (2011.01)
  *B82Y 40/00* (2011.01)
  *G01N 33/483* (2006.01)
  *G01N 33/553* (2006.01)
(52) U.S. Cl.
  CPC ......... *G01N 33/483* (2013.01); *G01N 33/553* (2013.01)

(56) References Cited

U.S. PATENT DOCUMENTS

| | | | |
|---|---|---|---|
| 2008/0096289 A1 | 4/2008 | Zhou et al. | |
| 2009/0140206 A1* | 6/2009 | Nie | B82Y 30/00 |
| | | | 252/301.16 |
| 2010/0177306 A1 | 7/2010 | Natan | |
| 2013/0115717 A1* | 5/2013 | Guo | G01N 33/54346 |
| | | | 422/69 |

OTHER PUBLICATIONS

International Search Report in PCT/KR2019/012072 (Jun. 4, 2020).
Written Opinion in PCT/KR2019/012072 (Jun. 4, 2020).
Notice of Allowance of Korean Patent Application No. 10-2019-0110212—6 pages (Apr. 21, 2021).

* cited by examiner

RAMAN-ACTIVE PARTICLE FOR SURFACE-ENHANCED RAMAN SCATTERING AND METHOD OF PRODUCING THE SAME

TECHNICAL FIELD

The present invention relates to a Raman-active particle for surface-enhanced Raman scattering and a method of producing the same, and more particularly, to a Raman-active particle which allows detection at a single molecule level and may be mass-produced by a simple process, and a method of producing the same.

BACKGROUND ART

Surface-enhanced Raman scattering (hereinafter, referred to as SERS) spectrometry is spectrometry using a phenomenon in which a Raman scattering intensity rapidly increases $10^6$ to $10^8$ times or more when molecules are adsorbed on a surface of a metal nanostructure such as gold and silver. The SERS spectrometry fused with nanotechnology, which currently develops at a very rapid pace, is particularly expected a lot to be critically used as a medical sensor.

As an example, since the SERS spectrometry is measurement technology having a high selectivity and high informativity, and simultaneously, is a powerful analysis method for chemical/biological/biochemical analysis of ultrahigh sensitivity, a study for performing early diagnosis of various diseases including Alzheimer's disease, diabetes, or the like, together with high-sensitivity DNA analysis, using SERS spectroscopy, is currently being actively conducted.

However, though SERS spectrometry has high selectivity, high informativity, and high sensitivity, signal enhancement changes very sensitively depending on the size or type of a gap or a junction between plasmon metals, a distance between a hot spot and a Raman signal generation source, and the like, and thus, reliability and reproducibility of measurement are deteriorated.

Thus, in order to be utilized in the biofields such as early diagnosis of diseases, development of a Raman-active particle which has high sensitivity to allow detection at a single molecule level and in which reliable and reproducible surface-enhanced Raman scattering occurs should be preceded, and development of technology of mass-producing the Raman-active particle within a short time should be also preceded.

DISCLOSURE

Technical Problem

An object of the present invention is to provide a Raman-active particle which has strictly defined hot spots, represents uniform Raman activity based on one particle, and simultaneously represents uniform Raman activity between particles, thereby allowing reproducible and reliable quantitative detection.

Another object of the present invention is to provide a Raman-active particle having extremely good sensitivity to allow detection at a single molecule level.

Another object of the present invention is to provide a Raman-active particle having biocompatibility to be suitable for biosensing such as disease detection.

Another object of the present invention is to provide a method of producing Raman-active particles which allow reproducible and reliable detection and have extremely good sensitivity.

Still another object of the present invention is to provide a method of producing Raman-active particles having very good commerciality so that the particles may be mass-produced at room temperature within a short time by a simple method.

Technical Solution

In one general aspect, a Raman-active particle includes: a spherical plasmonic metal core; a plasmonic metal shell having surface unevenness; and a self-assembled monolayer which is bonded to each of the core and the shell and positioned between the core and the shell, and includes a Raman reporter.

In the Raman-active particle according to an exemplary embodiment of the present invention, the plasmonic metal shell may include plasmonic metal fine particles having an average size of 0.1 D to 0.6 D, based on a diameter (D) of the metal core, and may have surface unevenness due to the plasmonic metal fine particles.

In the Raman-active particle according to an exemplary embodiment of the present invention, the plasmonic metal core and the plasmonic metal shell may be independently of each other one or more metals selected from gold, silver, platinum, palladium, nickel, aluminum, and copper.

In the Raman-active particle according to an exemplary embodiment of the present invention, the Raman-active particle may further include a receptor which is fixed to the plasmonic metal shell and bonded to an analyte.

In the Raman-active particle according to an exemplary embodiment of the present invention, the self-assembled monolayer may have a thickness of 0.5 to 2.0 nm.

In the Raman-active particle according to an exemplary embodiment of the present invention, in the plasmon metal shell, an inner shape of the shell in contact with the self-assembled monolayer may be spherical.

In the Raman-active particle according to an exemplary embodiment of the present invention, the plasmon metal core may have an average diameter of 20 to 100 nm.

The Raman-active particle according to an exemplary embodiment of the present invention may be for near-infrared excitation light having a wavelength of 750 nm or more.

The Raman-active particle according to an exemplary embodiment of the present invention may have a standard deviation of Raman signal intensity of 8.0 or less.

In another general aspect, a method of producing Raman-active particles includes: a) forming a self-assembled monolayer including a Raman reporter in a spherical plasmonic metal core; and b) using a reaction solution in which a buffer solution, the metal core on which the self-assembled monolayer is formed, and a plasmonic metal precursor are mixed, to form a plasmonic metal shell which surrounds the metal core on which the self-assembled monolayer is formed and has surface unevenness.

In the method of producing Raman-active particles according to an exemplary embodiment of the present invention, the plasmonic metal in the plasmonic metal precursor may be one or two or more selected from gold, silver, platinum, palladium, nickel, aluminum, and copper.

In the method of producing Raman-active particles according to an exemplary embodiment of the present invention, a mole ratio obtained by dividing the number of moles of a buffer of the buffer solution by the number of moles of the plasmonic metal precursor may be 10 to 100.

In the method of producing Raman-active particles according to an exemplary embodiment of the present invention, a molar concentration of the buffer of the buffer solution may be 10 to 200 mM.

In the method of producing Raman-active particles according to an exemplary embodiment of the present invention, the buffer solution may include one or more selected from 4-(2-hydroxyethyl)-1-piperazineethanesulfonic acid (HEPES), 4-(2-hydroxyethyl)piperazine-1-ethanesulfonic acid (MES), phosphated buffered saline (PBS), tris(2-amino-2-hydroxymethylpropne-1,3-idol), phosphate buffer (PB), 3-(N-morpholino)propanesulfonic acid (MOPS), 3-[[1,3-dihydroxy-2-(hydroxymethyl)propan-2-yl]amino]propane-1-sulfonic acid (TAPS), and piperazine-N,N'-bis(2-ethanesulfonic acid) (PIPES).

In the method of producing Raman-active particles according to an exemplary embodiment of the present invention, the metal core may have a diameter of 20 to 100 nm.

The method of producing Raman-active particles according to an exemplary embodiment of the present invention may further include c) fixing a receptor bonding to an analyte to the metal shell, after step b).

In another general aspect, Raman-active particle produced from the production method described above are provided.

In still another general aspect, a method of detecting an analyte using the Raman-active particles described above is provided.

The detection method according to the present invention includes bringing the Raman-active particles described above into contact with the analyte and irradiating excitation light thereon.

Advantageous Effects

The Raman-active particle according to an exemplary embodiment of the present invention has a core-shell structure of a spherical plasmon active core and a plasmon active shell having surface unevenness due to fine particles. In addition, the Raman-active particle has hot spots which have strictly defined size and shape and are uniformly present in the whole area of the particle, by the self-assembled monolayer including a Raman reporter positioned between the core and the shell, the spherical core shape, and the shell surrounding the self-assembled monolayer to have a spherical inner surface. In addition, the Raman-active particle has a Raman reporter positioned uniformly at a high density in the form of the self-assembled monolayer, in the area of the hot spots which are well defined and present uniformly and continuously in the whole area of the particle. In addition, since in the metal shell, metal fine particles themselves protrude and form bumpy unevenness on the whole area of a metal shell surface, sensitivity may be greatly improved without inhibiting uniformity of isotropic Raman activity in the particle and Raman activity between the particles. Due to the characteristics and structure of the Raman-active particle as such, the Raman-active particle according to an exemplary embodiment of the present invention has uniform Raman activity based on the particle, and has little deviation of Raman activity between the particles, thereby allowing reproducible quantity detection and having excellent detection ability at a single molecule level.

In addition, since the Raman-active particles according to an exemplary embodiment of the present invention have well-defined hot spots continuously in the whole area of the particle, and a Raman reporter is uniformly positioned at a high density in the well-defined hot spots, a biochemical material (biomaterial) having a several to dozens of micrometers in size may be also reproducibly detected.

In addition, the Raman-active particles according to an exemplary embodiment of the present invention allow detection of a material by near-infrared irradiation of 750 nm or more and may prevent damage of a biological sample by excitation light irradiation for Raman analysis.

In addition, the Raman-active particle according to an exemplary embodiment of the present invention has a high Raman signal intensity and simultaneously hardly produces basal fluorescence, when a near-infrared ray of 750 nm or more is irradiated as excitation light, and thus, the particle is free from Raman signal distortion due to post-processing of a detection signal to have high detection reliability.

In addition, the Raman-active particle according to an exemplary embodiment of the present invention is free from a surfactant, and thus, has a characteristic of having biocompatibility.

In addition, in the Raman-active particle according to an exemplary embodiment of the present invention, an organic constituent component including a Raman reporter is protected by being wrapped by a shell, and the self-assembled monolayer-metal shell of a core-Raman reporter is strongly bonded by a functional group, and thus, the Raman-active particle has very good durability and physical/chemical stability.

In addition, the method of producing Raman-active particle according to an exemplary embodiment of the present invention is an extremely simple method of mixing a buffer solution, a metal precursor, and a spherical core metal at room temperature, and the Raman-active particles having the merits described above may be mass-produced within a short time.

DESCRIPTION OF DRAWINGS

The above and other objects, features and advantages of the present invention will become apparent from the following description of preferred embodiments given in conjunction with the accompanying drawings, in which.

BEST MODE

Figure 1:
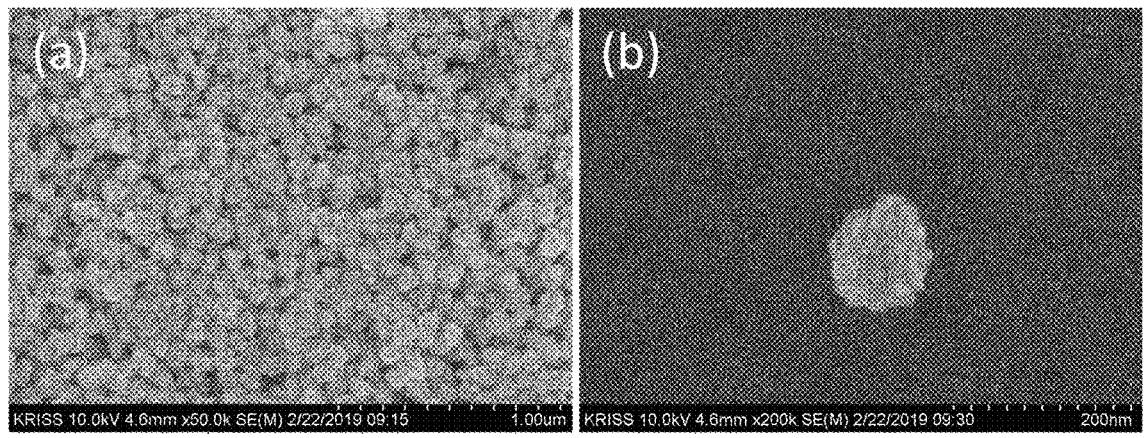
FIG. 1 is scanning electron micrographs of Raman-active particles produced according to an exemplary embodiment of the present invention at a low magnification (a) and at a high magnification (b).

Hereinafter, the Raman-active particle of the present invention and a method of producing the same will be described in detail with reference to the accompanying drawings. The drawings to be provided below are provided by way of example so that the idea of the present invention can be sufficiently transferred to a person skilled in the art to which the present invention pertains. Therefore, the present invention is not limited to the drawings provided below but may be embodied in many different forms, and the drawings suggested below may be exaggerated in order to clear the spirit of the present invention. Technical terms and scientific terms used herein have the general meaning understood by those skilled in the art to which the present invention pertains unless otherwise defined, and a description for the known function and configuration which may unnecessarily obscure the gist of the present invention will be omitted in the following description and the accompanying drawings. In addition, the singular form used in the specification and claims appended thereto may be intended to also include a plural form, unless otherwise indicated in the context. Units used in the present specification and attached claims thereto without particular mention are based on weights, and as an example, a unit of % or ratio refers to a wt % or a weight ratio.

The Raman-active particle according to the present invention is a Raman-active particle for surface-enhanced Raman scattering (SERS) and includes: a spherical plasmonic metal core; a plasmonic metal shell having surface unevenness; and a self-assembled monolayer which is bonded to each of the core and the shell and positioned between the core and the shell, and includes a Raman reporter.

The self-assembled monolayer positioned between the core and the shell has a strictly adjusted thickness due to the characteristics of self-assembly. Thus, a strictly defined nanogap having a size corresponding to the thickness of the self-assembled monolayer may be formed between the core and the shell. In addition, nanogaps (hot spots) having a uniform size may be formed in a whole area of the Raman-active particle by the structure of core-self-assembled monolayer-shell.

In addition, since the shape of the plasmonic metal core is spherical, the self-assembled monolayer has a spherical shape, and in the plasmonic metal shell, the inner shape of the metal shell in contact with the self-assembled monolayer may also have a spherical shape. Thus, nanogaps (hot spots) may be positioned in the whole area of the Raman-active particle, and simultaneously, the nanogaps (hot spots) may be positioned in the same well-defined position in all directions based on a radiation direction.

In addition, since the self-assembled monolayer positioned between the core and the shell contains the Raman reporter, the Raman reporter is positioned in the well-defined and same position in the radiation direction in the Raman-active particle, the Raman reporter is positioned uniformly at a high density in the whole area of the Raman-active particle, and also, the Raman reporter is positioned in the hot spot.

The Raman-active particle may represent uniform SERS activity based on the particle, have little deviation of the Raman activity between particles to represent uniform SERS activity between particles, and achieve larger Raman signal enhancement.

As a specific example of uniform SERS activity, a standard deviation (a.u.) of a Raman signal intensity (a maximum intensity of one Raman signal, a.u.) on a Raman spectrum of the Raman-active particles may be 8.0 or less. Here, the Raman spectrum of the Raman-active particles may be obtained by irradiating near-infrared light, using a known kind of Raman spectroscope. As an example, Raman spectroscopic analysis may be performed under the conditions of a laser at 780 nm, a laser power of 5 mW, an N.A. 0.75 object lens, and a laser exposure time of 1 second. The standard deviation may be calculated from the Raman spectrum of 50 or more Raman-active particles, but is not necessarily limited thereto.

As a specific example, each of the plasmon metal core and the plasmon metal shell may be a metal generating surface plasmon by an interaction with light. As an example, each of the plasmon metal core and the plasmon metal shell may be gold, silver, platinum, palladium, nickel, aluminum, copper, a mixture thereof, an alloy thereof, or the like. However, each of the plasmon metal core and the plasmon metal shell may be gold or silver, considering biocompatibility.

As a specific example, the plasmonic metal shell may include plasmonic metal fine particles having an average size of 0.1 D to 0.6 D, based on a diameter (D) of the metal core, and may have surface unevenness due to the plasmonic metal fine particles. Specifically, the metal shell in the state of being bonded to the self-assembled monolayer may be composed of metal fine particles having an average size of 0.1 D to 0.6 D, based on a diameter (D) of the metal core, and the metal shell may have irregular unevenness due to the particle shape of the metal fine particles.

An unevenness structure due to the metal fine particles of the plasmonic metal shell may form the hot spots on the surface of the shell itself, together with the hot spots by the nanogaps of the metal core and the metal shell, and thus, is more advantageous for signal enhancement. In addition, since in the metal shell, the metal fine particles themselves protrude to form bumpy unevenness in the whole area of the metal shell, the sensitivity of the Raman-active particle may be increased by the metal shell, uniform Raman activity may be represented in one particle, and also, uniformity of Raman activity between particles may not be inhibited.

An average diameter of the plasmon metal core may be in the level of 20 to 100 nm, specifically 20 to 80 nm, and more specifically 30 to 70 nm, but is not limited thereto.

In a specific example, the self-assembled monolayer may be a self-assembled monolayer of the Raman reporter. The Raman reporter may refer to an organic compound (organic molecule) including a Raman-active molecule, or an organic compound (organic molecule) having a bonding force to the metal of the metal core and including a Raman-active molecule. The Raman reporter is previously known in the art, and may be any one as long as it is widely used in the art.

Since the Raman reporter (molecule) has a bonding force to the metal of the metal core, the self-assembled monolayer of the Raman reporter may be formed on the metal core where a pure metal surface is exposed.

The Raman-active molecule may include a surface-reinforced Raman-active molecule, a surface-enhanced resonance Raman-active molecule, a hyper-Raman-active molecule, or a coherent anti-stokes Raman-active molecule. The Raman-active molecule may have both a Raman signal and a fluorescent signal, or have a Raman signal.

As a specific example, the Raman-active molecule may be selected from a group consisting of cyanines, fluorescein, rhodamine, 7-nitrobenz-2-oxa-1,3-diazole (NBD), phthalic acids, terephthalic acids, isophthalic acids, cresyl fast violet, cresyl blue violet, brilliant cresyl blue, paraaminobenzoic acid, erythrosin, biotin, dioxigenin, phthalocyanine, azomethine, xanthine, N,N-diethyl-4-(5'-azobenzotriazolyl)-phenylamine, aminoacridine, and a combination thereof. Examples of cyanine may include Cy3, Cy3.5, or Cy5. Examples of fluorescein may include carboxyfluorescein (FAM), 6-carboxy-2',4,4',5',7,7'-hexachlorofluorescein (HEX), 6-carboxy-2',4,7,7'-tetrachlorofluorescein (TET), 5-carboxy-4',5'-dichloro-2',7'-dimethoxyfluorescein, 6-carboxy-4',5'-dichloro-2'-7'-dimethoxyfluorescein (Joe), 5-carboxy-2',4',5',7'-tetrachlorofluorescein, 5-carboxyfluorescein, or succinylfluorescein. Examples of rhodamine may include tetramethylrhodamine (Tamra), 5-carboxyrhodamine, 6-carboxyrhodaminerhodamine, 6G (rhodamine 6G: R6G), tetramethyl rhodamine isothiol (TRIT), sulforhodamine 101 acid chloride (Texas Red dye), carboxy-X-rhodamine (ROX), or Rhodamine B.

As another specific example, the Raman-active molecule may be a Raman-active molecule in the form of a benzene ring, and the Raman-active molecule in the form of a benzene ring may include 4-aminothiophenol (4-ATP), 4-mercaptobenzoic acid (4-MBA), phenyl isothiocyanate (PITC), benzenethiol (BT), 1,4-benzenedithiol (BDT), biphenyl-4,4'-dithiol (BPDT), p-terphenyl-4,4"-dithiol (TPDT), 4-bromobenzenethiol (4-BBT), 4-chlorobenzenethiol (4-CBT), 3,3'-diethylthiatricarbocyanine iodide (DTTC), and the like.

However, since nanogaps (hot spots) are formed between the metal core and the metal shell by the Raman reporter bonded to the metal core, a length (size) of the Raman reporter may be 3 nm or less, specifically 0.5 to 2 nm, in terms of forming hot spots where stronger signal enhancement is done. Here, the length (size) of the Raman reporter corresponds to the thickness of the self-assembled monolayer, of course.

In addition, the Raman reporter includes the Raman-active molecule, but preferably has a first functional group which is spontaneously bonded to the metal core. More preferably, the Raman reporter has the first functional group which is spontaneously bonded to the metal of the metal core and a second functional group which is spontaneously bonded to the metal of the metal shell. In this case, the self-assembled monolayer is bonded to each of the metal core and the metal shell, thereby greatly improving a bonding force between the metal shell and the metal core to which the Raman reporter is fixed.

The functional group (the first functional group or the second functional group) may be any functional group as long as it is spontaneously bonded to the corresponding metal, considering the metals of the core and the shell. As a substantial example, when a first metal and a second metal are independently of each other gold or silver, the functional group (the first functional group or the second functional group) may be a thiol group (—SH), a carboxyl group (—COOH), an amine group (—NH$_2$), or the like, but the present invention is not limited to the specific kinds of functional group.

The Raman-active molecule having a bonding force to the metal of the metal core by the first functional group is spontaneously bonded (fixed) to the metal core, whereby the self-assembled monolayer of the Raman reporter may be formed on the metal core, and a film of the Raman reporter having a uniform thickness may be homogeneously formed on the whole surface of the metal core.

In a specific example, the Raman-active particle may further include a receptor which is fixed to the plasmonic metal shell and bonded to an analyte. The receptor may be any material known to be specifically bonded to the analyte, such as complementary bonding between enzyme-substrate, antigen-antibody, protein-protein, or DNA-DNA. Here, the receptor may include a functional group which is spontaneously bonded to the metal of the metal shell (as an example, a thiol group, a carboxyl group, an amine group, or the like), and may be in the state of being spontaneously and chemically bonded to the metal shell by the functional group.

In a specific example, the Raman-active particle may further include a blocking molecule covering a surface area of the shell to which the receptor is not attached (bonded). The blocking molecule prevents an undesired interaction between the analyte and the shell surface itself, not the receptor, and may serve to make orientation of the receptor positioned on the surface of the shell more constant. The blocking molecule may be any material which is commonly used for preventing nonspecific bonding on the bare metal surface in the biosensor field, such as bovine serum albumin (BSA).

The analyte may be a material derived from the living (including a virus) or non-living thing. The living thing-derived material may include a cell component. Specifically, the analyte may include a lesion biomarker, a pathogen, a protein, a nucleic acid, a sugar, a drug, and the like. More specifically, the analyte may be an amino acid, a peptide, a polypeptide, a protein, a glycoprotein, lipoprotein, nucleoside, nucleotide, oligonucleotide, a nucleic acid, a sugar, a carbohydrate, an oligosaccharide, a polysaccharide, a fatty acid, a lipid, a hormone, a metabolite, a cytokine, a chemokine, a receptor, a nucleotransmitter, an antigen, an allergen, an antibody, a substrate, a metabolite, a cofactor, an inhibitor, a drug, a pharmaceutical material, a nutritional substance, a prion, a toxin, a poisonous material, an explosive material, an insecticide, a chemical weapon agent, a biohazard agent, a radioactive isotope, a vitamin, a heterocyclic aromatic compound, a carcinogen, a mutagen, an anesthetic, an amphetamine, a barbiturate, a hallucinogen, waste, or a pollutant. In addition, when the analyte is a nucleic acid, the nucleic acid may include genes, viral RNA and DNA, bacterial DNA, fungal DNA, mammalian DNA, cDNA, mRNA, RNA and DNA fragments, oligonucleotides, synthetic oligonucleotides, modified oligonucleotides, single- and double-stranded nucleic acids, natural and synthetic nucleic acid, and the like.

The analyte may be positioned in-vivo, and may be detected in-vivo. That is, the Raman-active particle described above may be for use in-vivo, and for biological injection.

On the contrary, the analyte may be positioned in-vitro, and may be detected in-vitro. That is, the Raman-active particle described above may be used in-vitro. Here, the analyte may be in the form of a sample collected in-vivo such as blood, urine, mucosal detachment, saliva, body fluids, tissues, biopsy materials, a combination thereof, or the like, but is not limited thereto.

In a specific example, the Raman-active particle may be for near-infrared excitation light having a wavelength of 750 nm or more, specifically a near-infrared ray having a wavelength of 750 to 1500 nm, and more specifically, for near-infrared excitation light having a wavelength of 750 to 1000 nm, a wavelength of 770 nm to 1500 nm, or a wavelength of 780 nm to 1000 nm. That is, the Raman-active particle allows detection and analysis of the analyte by light irradiation in a near-infrared region.

As is known, when visible light is irradiated on a biomaterial including a biochemical material, a fluorescence phenomenon may occur. Since fluorescence intensity is very strong as compared with Raman scattering and fluorescence occurs in a similar region to Raman scattering, it is difficult to obtain pure Raman spectrum covered with a fluorescence peak. Therefore, SERS analysis by light irradiation in a near-infrared region, not a visible region, may obtain a Raman spectrum without an influence of fluorescence, and thus, is very advantageous in a biofield.

Substantially, when the analyte is detected using the Raman-active particles according to a specific example, basal fluorescence may not be substantially shown on a Raman spectrum of the analyte obtained by near-infrared irradiation.

However, the Raman-active particle of the present invention should not be interpreted limitedly as being used for a near-infrared ray, and excitation light irradiated in the detection method of the present invention should not be interpreted limitedly as being a near-infrared ray. As an example, based on the center wavelength ($\lambda_{max}$) of a maximum absorption peak in a UV-visible light absorption spectrum of the Raman-active particles, light in a wavelength region of the center wavelength ($\lambda_{max}$)±150 nm, the center wavelength ($\lambda_{max}$)±100 nm, or the center wavelength ($\lambda_{max}$)±50 nm may be irradiated as excitation light, and in this case, a Raman spectrum in which larger Raman signal enhancement is formed may be obtained. In an exemplary embodiment, light in a wavelength region of 500 to 750 nm, 500 to 750 nm, 550 to 700 nm, or 600 to 680 nm may be irradiated as the excitation light.

The present invention includes a method of detecting an analyte using the Raman-active particles described above.

The detection method according to the present invention includes bringing the Raman-active particles into contact with an analyte and irradiating excitation light thereon. Here, in the Raman-active particle, a receptor (first receptor) which may be specifically bonded to the analyte may be formed on the surface of the particle. Here, the excitation light may be light in a visible to near-infrared region, and the visible light may be light in a wavelength region of the center wavelength ($\lambda_{max}$)±150 nm, based on the center wavelength ($\lambda_{max}$) of a maximum absorption peak in a UV-visible light absorption spectrum of the Raman-active particles.

As a specific example, the detection method may include a first step of bringing a sample into contact with an active surface on which a receptor (second receptor) which may be specifically bonded to an analyte; a second step of bringing the Raman-active particles into contact with the active surface in contact with the sample; and a third step of irradiating the active surface in contact with the Raman-active particles with excitation light to obtain Raman mapping. The second receptor may be specifically bonded to the analyte, and when the analyte is present in the sample, the analyte may be fixed to the active surface by the second receptor. Here, the first receptor and the second receptor are specifically bonded to different sites from each other of the analyte, of course.

Contacting in the first step may be performed by applying a liquid sample on the active surface or immersing the active surface in the liquid sample, and after a sufficient time for the analyte which may be present in the sample to be stably bonded to the second receptor has passed, the applied liquid sample may be removed.

Contacting in the second step may be performed by applying a Raman-active particle dispersion solution on the active surface in contact with the sample, or immersing the active surface in the Raman-active particle dispersion solution, and after a sufficient for the Raman-active particles to be stably bonded to the analyte fixed to the active surface has passed, unreacted Raman-active particles may be removed.

By the second step, the Raman-active particles are specifically bonded to the analyte fixed to the active surface, thereby forming a bonding structure of active surface-second receptor-analyte-Raman-active particles.

In the third step, excitation light (irradiation light) may be a near-infrared ray having a wavelength of 750 nm or more, specifically a near-infrared ray in a wavelength region of 750 nm to 1500 nm, a wavelength region of 750 nm to 1000 nm, a wavelength region of 770 nm to 1500 nm, or a wavelength region of 780 nm to 1000 nm.

The Raman mapping may be Raman mapping to an area having a predetermined size, and the predetermined size may be 1 to 100 μm×1 to 100 μm, but is not limited thereto. In addition, a mapping interval in the Raman mapping may be in a level of 0.1 μm to 10 μm to each of axes perpendicular to each other, an output of excitation light (excitation laser light) may be in a level of 1 mW to 90 mW, as a practical example, 1 mW to 10 mW, an excitation light irradiation time may be 0.5 to 10 seconds, and the number of scanning may be 1 to 5, but are not limited thereto.

In a specific example, the detection method may further include a fourth step in which after the third step, one peak of Raman peaks by the Raman reporter of the Raman-active particles (hereinafter, referred to as a first peak) is selected, and intensities of the corresponding one peak (first peak) on the Raman mapping are summed up to quantify a concentration of a substance to be detected. Here, the intensities to be summed up may be maximum intensity values of the Raman signal (peak value).

That is, quantitative analysis of the substance to be detected is possible only by summing up the intensities of certain Raman peaks (first peaks) present on the Raman mapping, by the Raman-active particles having isotropic SERS activity, highly uniform SERS activity between the Raman-active particles, substantially no occurrence of basal fluorescence, reliability representing an excellent Raman signal intensity, and the like, and a limit of detection is in a level of 20 aM, and thus, the sensitivity is extremely high so that even a single substance to be analyzed may be detected.

Substantially, in a semi-log graph in which a log value of a molar concentration of the substance to be detected (analyte) is represented in the x-axis, and the sum of Raman signal intensities (a.u.) of certain Raman peaks (first peaks) is represented in the y-axis, the log value of the molar concentration (MC) of the substance to be detected and the sum of the Raman signal intensities ($I_{sum}$) are in a straight line relationship. That is, in the semi-log graph, MC=$aI_{sum}$+b (each of a and b is a constant. Here, this linearity may be maintained in a wide range of molar concentrations of $10^{-2}$ fM to $10^6$ fM.

Thus, the detection method may further include performing the Raman mapping using standard samples containing a substance to be detected at a predetermined molar concentration, and obtaining the sum of Raman signal intensities in a certain Raman signal at the corresponding concentration to obtain a standard graph which is a relation between the molar concentration and the sum of the Raman signal intensities on the semi-log graph, and by putting the intensity calculated in the fourth step (summed intensity) on the standard graph, the amount of the substance to be detected in the sample may be quantitatively analyzed.

The Raman spectrum may be obtained using a common Raman detection device. As a non-limiting example, the excitation light passes through a confocal optical instrument and a microscope lens to be focused on the active surface. When the analyte is present on the active surface, Raman light emitted from the analyte may be focused by the microscope lens and the confocal optical instrument and combined with a monochromatic light device for spectrum separation. The Raman signal may be detected by a Raman detector connected by an interface to a computer in which signals are counted and digitalized.

The present invention includes a method of producing the Raman-active particle. Hereinafter, the production method according to the present invention will be described in detail. Here, the metal core, the Raman reporter, the self-assembled monolayer, the metal shell, the analyte, the receptor, and the like are similar or identical to those described above for the Raman-active particle. Thus, the method of producing Raman-active particles according to the present invention includes all described above for the Raman-active particle.

The method of producing Raman-active particles according to the present invention is a method of producing Raman-active particles for surface-enhanced Raman scattering (SERS). The production method according to the present invention includes: a) forming a self-assembled monolayer including a Raman reporter in a spherical plasmonic metal core; and b) using a reaction solution in which a buffer solution, the metal core on which the self-assembled monolayer is formed, and a plasmonic metal precursor are mixed, to form a plasmonic metal shell which surrounds the metal core on which the self-assembled monolayer is formed and has surface unevenness.

The method of producing Raman-active particles according to the present invention may mass-produce Raman-active particles having reproducibility and reliability, a sensitivity allowing a single molecule detection, and biocompatibility without a separate post-treatment at low cost, by a simple process.

As is known, for metal nanogranulation and designed shaping, an organic surfactant which may suppress growth, derive growth in a certain direction, and/or stabilize nanoparticles while providing appropriate reducibility is used in a well-known or commonly used art, and also, an organic acid or an organic acid which may substitute a surfactant is used. However, the metal nanoparticles synthesized by the method have an organic surfactant which is harmful to a living body and may affect a biochemical material, bonded thereto. Thus, in order to be used in the biofield, a post-treatment process such as capping particles by a capping material having biocompatibility or substituting a harmful surface functional group of an organic surfactant or the like with another functional group having biocompatibility is necessarily required.

However, capping using the capping material may greatly decrease the intensity of biosensing or bioimaging based on SERS spectroscopy, and when the organic surfactant is to be substituted with a biocompatible functional group, it is difficult to completely substitute the organic surfactant which is bonded to a metal material with a very strong bonding force, and thus, toxicity still remains.

Since in the method of producing Raman-active particles according to the present invention described above, a self-assembled monolayer having a Raman reporter is formed on a metal core having a bare metal surface, and then a buffer solution which already has biocompatibility and a solution containing a metal precursor are used to form a metal shell, the Raman-active particle produced is free from the organic surfactant which is harmful to a living body to have biocompatibility immediately after production.

Accordingly, in the method of producing Raman-active particles according to an exemplary embodiment of the present invention, the reaction solution may not contain a surfactant (organic surfactant), and furthermore, the reaction solution may not contain both the surfactant and the organic acid.

In addition, since in the method of producing Raman-active particles according to the present invention, the Raman-active particles are produced using a simple process of attaching the Raman reporter to the metal core and forming the metal shell using the buffer solution and the solution containing a metal precursor, the Raman-active particles may be mass-produced within a short time at low cost, and thus, the method has excellent commerciality.

In addition, since in the method of producing Raman-active particles according to the present invention, an organic material including the Raman reporter is not exposed to the surface of the Raman-active particle, but is surrounded by the metal shell, the organic substance to be detected including the Raman-active particle may be stably protected from an external environment.

In a specific example, a step of forming the self-assembled monolayer including the Raman reporter on the metal core (step (b)) may include preparing a mixed solution containing the metal core and the Raman reporter and ultrasonically stirring the solution.

Specifically, step a) may include a1) mixing the metal core and the Raman reporter so that the molar concentrations thereof are 0.01 to 1 nM and 10 to 1000 µM, to prepare a mixed solution; a2) ultrasonically stirring the solution to perform a reaction at room temperature for 10 to 30 minutes; and a3) separating and recovering the metal core to which the Raman reporter is fixed. Here, the mixed solution may be an aqueous mixed solution, but is not necessarily limited thereto.

After performing step a), b) forming the metal shell surrounding the metal core to which the Raman reporter is fixed from a reaction solution in which the buffer solution, the metal core to which the Raman reporter is fixed (metal core on which the self-assembled monolayer is formed), and the metal precursor, may be performed. The metal core to which the Raman reporter is fixed may be a metal core on which the self-assembled monolayer of the Raman reporter is formed.

In step b), the mole ratio of a buffer of the buffer solution and the metal precursor (mole ratio obtained by dividing the number of moles of the buffer by the number of moles of the metal precursor) may be 10 to 100, preferably 20 to 80. When the mole ratio is controlled to 10 to 100, preferably 20 to 80, a thin metal shell which completely surrounds the Raman reporter fixed to the metal core may be formed, and a metal shell having surface unevenness by metal fine particles may be formed.

The buffer solution may include one or more selected from 4-(2-hydroxyethyl)-1-piperazineethanesulfonic acid (HEPES), 4-(2-hydroxyethyl)piperazine-1-ethanesulfonic acid (MES), phosphated buffered saline (PBS), tris(2-amino-2-hydroxymethylpropne-1,3-idol), phosphate buffer (PB), 3-(N-morpholino)propanesulfonic acid (MOPS), 3-[[1,3-dihydroxy-2-(hydroxymethyl)propan-2-yl]amino] propane-1-sulfonic acid (TAPS), and piperazine-N,N'-bis(2-ethanesulfonic acid) (PIPES). The buffer of the buffer solution may serve as a weak reducing agent which reduces a metal, and allows a surfactant for stabilizing the produced Raman-active particles by the buffer of the buffer solution to be excluded.

The metal of the metal precursor may be gold, silver, platinum, palladium, nickel, aluminum, copper, a mixture thereof, an alloy thereof, or the like. However, the metal of the metal precursor may be preferably gold or silver, independently of the metal of the metal core, considering biostability. The metal precursor according to an advantageous example may be a gold precursor such as $HAuCl_4$, $HAuBr_4$, NaAuCl$_4$, AuCl$_3$O·3H$_2$O, NaAuCl$_4$·2H$_2$O, or a mixture thereof, or a silver precursor such as AgNO$_3$, but is not limited thereto.

In a specific example, in step b), the buffer solution, the metal precursor solution, and the metal core dispersion to which the Raman reporter is fixed are mixed to prepare the reaction solution, and the reaction is performed at a temperature of 15 to 40° C., specifically a temperature of 15 to 35° C., more specifically a temperature of 15 to 25° C., and still more specifically at room temperature (21 to 25° C.). The metal shell may be prepared by reacting the reaction solution for 10 minutes to 50 minutes, specifically 20 minutes to 40 minutes, but the present invention is not limited to the reaction time of the reaction solution. Here, stirring may be performed during the reaction, and the reaction may be completed by adding an excessive amount of water to the reaction solution.

The molar concentration of the buffer in the buffer solution may be 10 to 100 mM, the molar concentration of the metal precursor in the metal precursor solution may be 1 to 10 mM, and the molar concentration of the metal core in the metal core dispersion to which the Raman reporter is fixed may be 0.01 to 0.5 nM, but are not limited thereto.

The buffer solution and the metal precursor solution may be mixed so that the mole ratio between the buffer and the metal precursor described above are satisfied, and the metal core dispersion may be mixed so that the mole ratio of the metal precursor to metal core is 1:1×10$^{-7}$ to 1×10$^{-5}$. Here, the metal precursor solution and the metal core dispersion are first mixed, and then the buffer solution is mixed, so that the metal shell may be uniformly formed on the metal core(s).

Specifically, step b) may include b1) mixing the metal precursor solution and the metal core dispersion to prepare a precursor-metal core mixed solution; b2) mixing the buffer solution with the precursor-metal core mixed solution to prepare a reaction solution and reacting the reaction solution at a temperature of 15 to 40° C., advantageously at room temperature to prepare Raman-active particles; and b3) separating and recovering the produced Raman-active particles and adding the recovered Raman-active particles to a buffer solution (a separate buffer solution) to store the solution at a temperature of 1 to 10° C., specifically at a temperature of 1 to 5° C.

By step b), the Raman-active particles including the metal core, the self-assembled monolayer of the Raman reporter surrounding the metal core, and the metal shell surrounding the self-assembled monolayer may be produced, and the Raman-active particles may have an average size of 150 nm or less, substantially 100 nm or less, substantially 40 to 100 nm, and more substantially 60 to 100 nm.

In a specific example, the method of producing Raman-active particles may further include c) fixing a receptor which is bonded (specifically bonded) to an analyte to the metal shell, after step b). Step c) may be performed by mixing the receptor with the prepared Raman-active particle dispersion solution, and fixing may be performed depending on a protocol known for each receptor, of course.

In addition, before step a), a step of washing the metal core using an organic solvent and the like, so that the spherical metal core has a bare metal surface, may be performed, but the washing is enough to be performed if necessary.

The present invention includes the Raman-active particles produced from the production method described above.

FIG. 1 is scanning electron micrographs of the Raman-active particles produced according to an exemplary embodiment of the present invention at a low magnification (a) and at a high magnification (b).

Specifically, the Raman-active particles were produced by mixing spherical Au nanoparticles (diameter=50 nm) as a metal core with 1 mL of a 1 mM bis(p-sulfonatophenyl) phenylphosphine dihydrate dipotassium salt (BSPP) solution and sonicating the solution for 10 minutes to prepare an Au core dispersion solution having a molar concentration of 0.1 nM. 1 mL of an Au core dispersion solution and 50 μL of a 1,4-benzenedithiol (BDT) solution were mixed, sonicated for 10 minutes, and then centrifuged at 6000 rpm for 10 minutes to recover an Au core on which the self-assembled monolayer of BDT which is the Raman reporter. The recovered Au core on which a self-assembled monolayer was formed was dispersed in 1 mL of deionized water (molar concentration of 0.1 nM), 500 μL of 5 mM HAuCl$_4$ and 2.5 mL of a 50 mM HEPES buffer solution at pH 7.2 were added to the dispersion solution, the solution was stirred at 1000 rpm for 30 minutes, and an excessive amount of deionized water was added thereto to complete the reaction. Thereafter, centrifugation was performed at 4000 rpm, 3000 rpm, and 2000 rpm for 10 minutes to prepare the Raman-active particles, and the particles were recovered, added to 1 ml of a 50 mM HEPES buffer solution, and stored.

It was confirmed from FIG. 1 that Raman-active particles having a shell formed thereon, having surface unevenness formed by Au fine particles, were produced. The produced Raman-active particles had an average diameter of 95 nm, and the Au fine particles forming the shell had an average size of 22 nm. As shown in FIG. 1, it was found that Au fine particles protruded and surface unevenness was formed on the shell, and it was confirmed that unevenness by protrusion of the fine particles was evenly formed, in all directions based on a particle center.

Figure 2:
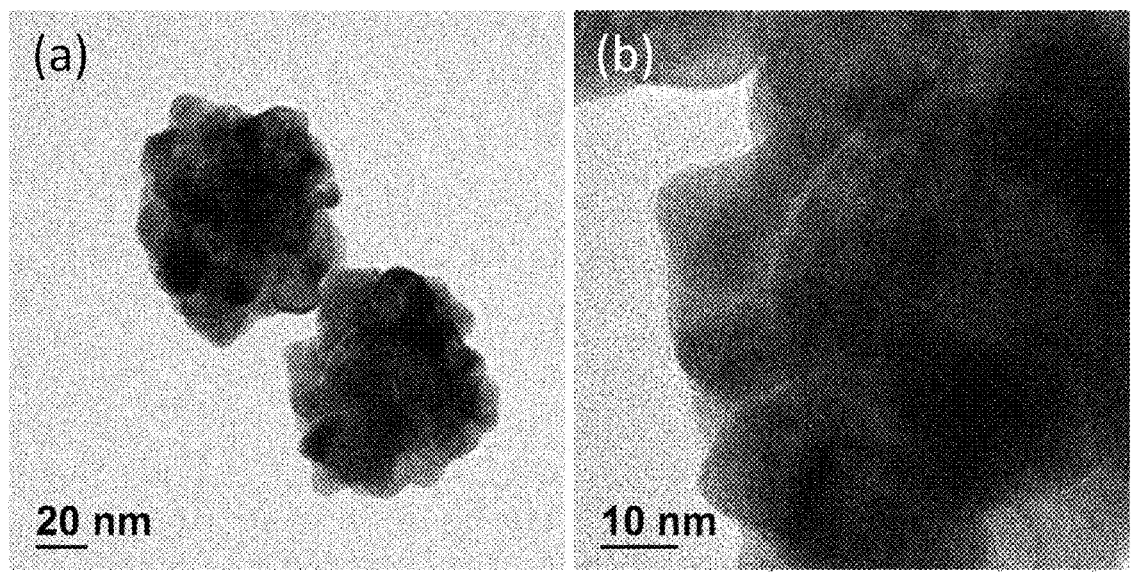
FIG. 2 is transmission electron micrographs of the Raman-active particles produced according to an exemplary embodiment of the present invention.

FIG. 2 is transmission electron micrographs of the Raman-active particle.

It was confirmed that the self-assembled monolayer of the Raman reporter was positioned between an Au core and an Au shell of a polycrystal composed of Au fine particles, and a nanogap having a thickness of 0.8 bn was formed in the whole area of the particle.

Figure 3:
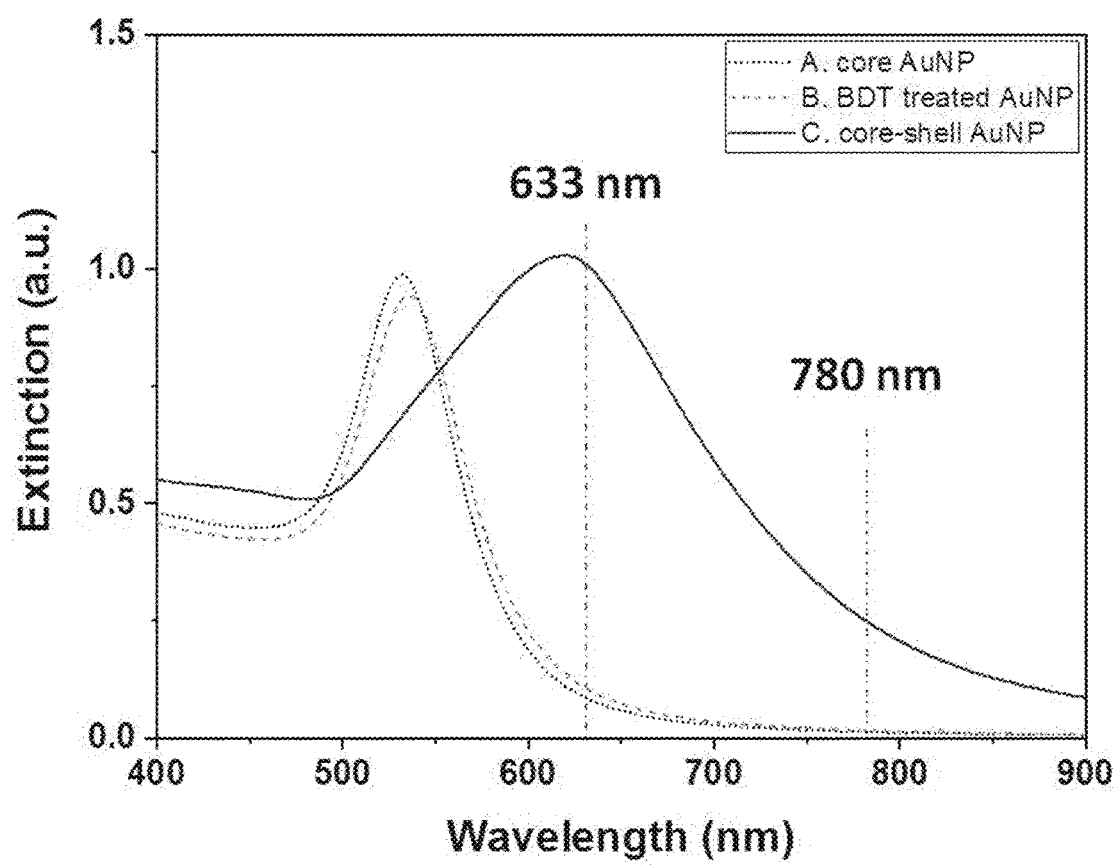
FIG. 3 is a drawing illustrating a UV-Vis absorption spectrum of each of an Au core itself (cpre AuNP in FIG. 3), an Au core on which a self-assembled monolayer is formed (BDT-treated AuNP in FIG. 3), and the Raman-active particles produced according to an exemplary embodiment of the present invention.

FIG. 3 is a drawing illustrating a UV-Vis absorption spectrum of each of an Au core itself (core AuNP in FIG. 3), an Au core on which a self-assembled monolayer is formed (BDT-treated AuNP in FIG. 3), and the produced Raman-active particles. As seen from FIG. 3, it was found that the Au core and the Au core on which the self-assembled monolayer was formed represented substantially almost similar absorption spectra, but the produced Raman-active particle had an absorption peak which was shifted to about 620 nm. In addition, unlike the Au core or the Au core on which the self-assembled monolayer was formed, the Raman-active particle had a very broad absorption peak of a half width of 200 nm or more. In addition, it was found that though the Raman-active particle had a very high absorbance around 620 nm, the particle also had a significant absorbance even at a near-infrared ray at 700 nm or more, specifically at 780 nm or more.

Figure 4:
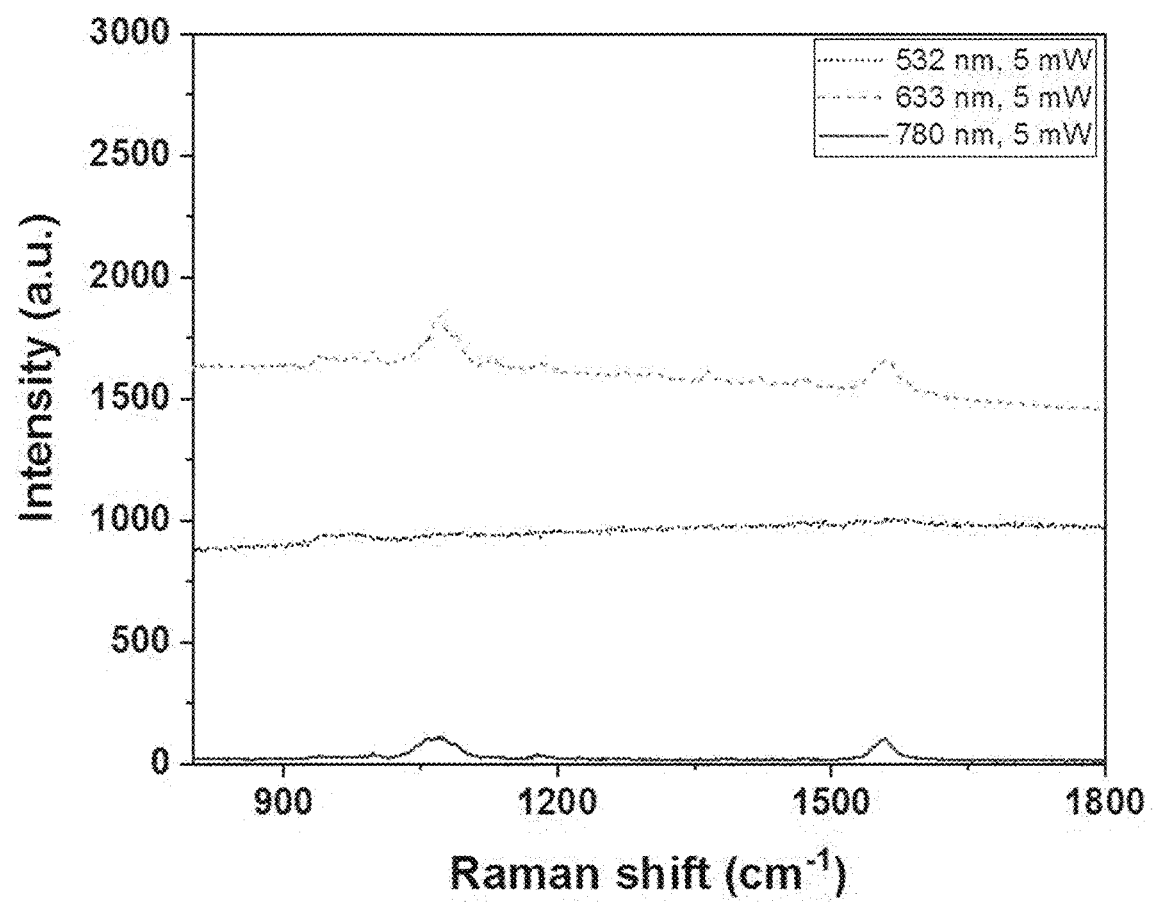
FIG. 4 is a drawing illustrating a measured Raman spectrum of the Raman-active particles themselves produced according to an exemplary embodiment of the present invention.

FIG. 4 is a drawing illustrating a Raman spectrum of measuring the produced Raman-active particles themselves, and the spectrum was obtained by irradiating a laser at 532 nm (5 mW), a laser at 633 nm (5 mW), or a laser at 780 nm (5 mW). As seen from FIG. 4, it was found that when light at 633 nm was irradiated, the highest intensity of Raman signal was obtained, but a strong Raman signal was still obtained even when near-infrared light at 780 nm was irradiated. In addition, as seen from FIG. 4, when light in a visible region was irradiated, very large basal fluorescence occurred. However, it was found that when near-infrared light at 780 nm was irradiated, any significant basal fluorescence to affect a detection signal did not occur. Thus, it was found that when Raman spectroscopic analysis was performed by irradiating the Raman-active particles according to a specific exemplary embodiment of the present invention with a near-infrared ray, the detected signal intensity may be immediately used as a Raman signal intensity without separate signal treatment, and reliable Raman analysis may be performed. As is known, a signal processing process for removing basal fluorescence may cause Raman signal distortion, which is problematic in quantitative analysis.

Figure 5:
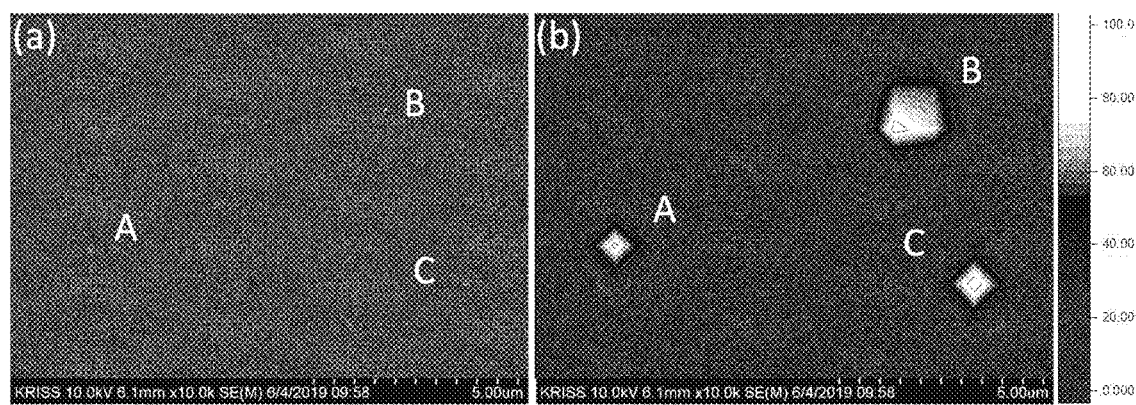
FIG. 5 is a scanning electron micrograph (a) of the Raman-active particles (A, B, and C) produced according to an exemplary embodiment of the present invention observed after positioning the particles on a silicon substrate, and a drawing illustrating Raman mapping (laser at 780 nm, 5 mW) (b) an area observed by a scanning electron microscope.

FIG. 5 is a scanning electron micrograph (a) of the Raman-active particles (A, B, and C) observed after positioning the particles on a silicon substrate, and a drawing illustrating Raman mapping (laser at 780 nm, 5 mW) in an area observed by a scanning electron microscope. As seen from FIG. 5, it was found that the produced Raman-active particles had uniform Raman activity.

Figure 6:
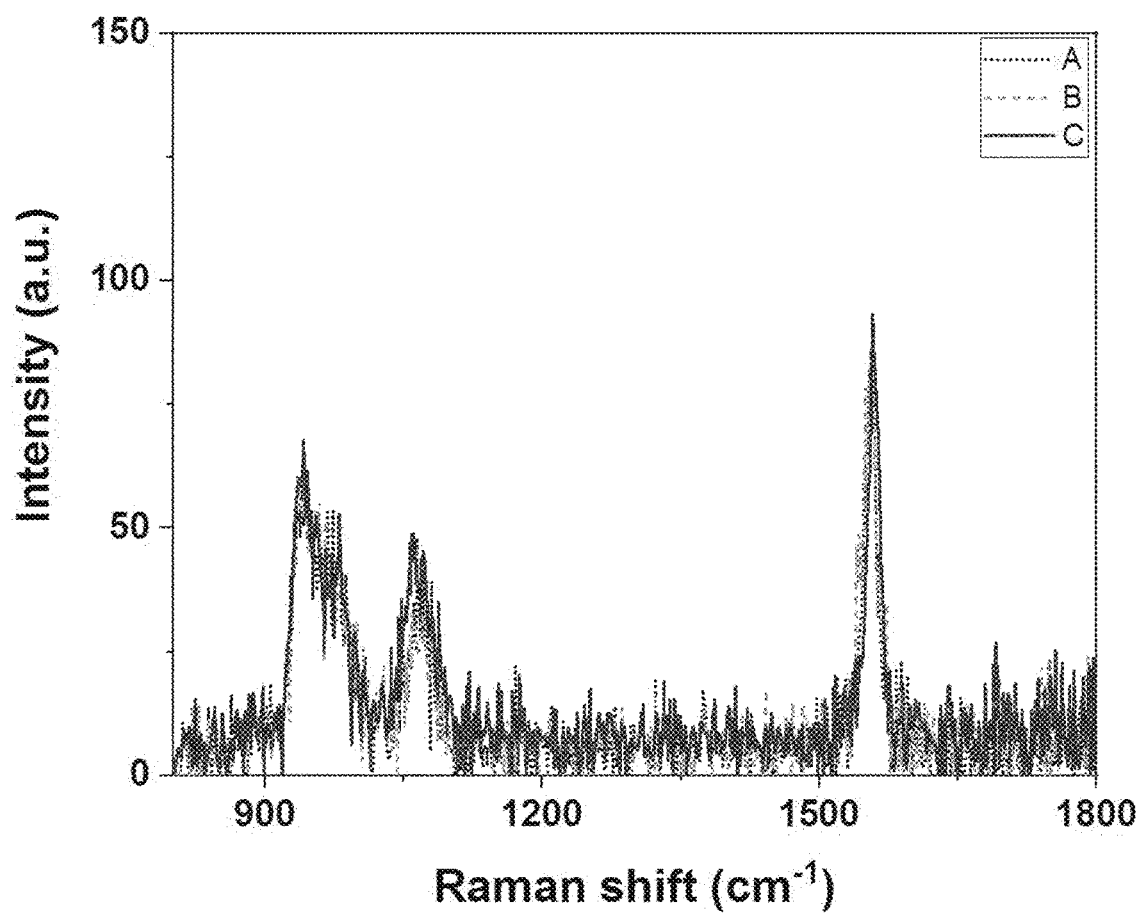
FIG. 6 is a drawing illustrating a Raman spectrum of each of the Raman-mapped Raman-active particles (A, B, and C) in FIG. 5 by overlapping.

FIG. 6 is a drawing illustrating a Raman spectrum of each of the Raman-mapped Raman-active particles (A, B, and C) in FIG. 5 by overlapping. As seen from FIG. 6, it was confirmed that the substantially the same Raman spectra between the Raman-active particles were obtained.

Similarly, a Raman spectrum of each Raman-active particle was obtained for 60 Raman-active particles produced and then an average value and a standard deviation of the peak intensity for one Raman peak were measured, and as a result, the average value was 87.6 (a.u.) and the standard deviation was 7.5 (a.u.), and thus, it was confirmed therefrom that extremely uniform Raman activity between particles was shown.

Hereinabove, although the present invention has been described by specific matters, limited exemplary embodiments, and drawings, they have been provided only for assisting the entire understanding of the present invention, and the present invention is not limited to the exemplary embodiments, and various modifications and changes may be made by those skilled in the art to which the present invention pertains from the description.

Therefore, the spirit of the present invention should not be limited to the above-described exemplary embodiments, and the following claims as well as all modified equally or equivalently to the claims are intended to fall within the scope and spirit of the invention.

The invention claimed is:

1. A Raman-active particle comprising:
a spherical plasmonic metal core;
a plasmonic metal shell having surface unevenness; and
a self-assembled monolayer which is bonded to each of the core and the shell and positioned between the core and the shell, and includes a Raman reporter,
wherein each of said plasmonic metal core and said plasmonic metal shell is a metal that configured to generate surface plasmon by interaction with light,
wherein the plasmonic metal shell includes plasmonic metal fine particles having an average size of 0.1 D to 0.6 D, based on a diameter (D) of the metal core, and has the surface unevenness due to the plasmonic metal fine particles,
wherein the Raman reporter includes a Raman-active molecule,
wherein the Raman-active molecule is 1,4-benzenedithiol (BDT), and
wherein a standard deviation of a Raman signal intensity is 8.0 or less.

2. The Raman-active particle of claim 1, wherein the plasmonic metal core comprises one or more metals selected from gold, silver, platinum, palladium, nickel, aluminum, and copper.

3. The Raman-active particle of claim 1, further comprising: a receptor which is fixed to the plasmonic metal shell and bonded to an analyte.

4. The Raman-active particle of claim 1, wherein the self-assembled monolayer has a thickness of 0.5 to 2.0 nm.

5. The Raman-active particle of claim 1, wherein in the plasmon metal shell, an inner shape of the shell in contact with the self-assembled monolayer is spherical.

6. The Raman-active particle of claim 1, wherein the plasmon metal core has an average diameter of 20 to 100 nm.

7. The Raman-active particle of claim 1, wherein the particle is for near-infrared excitation light having a wavelength of 750 nm or more.

8. A detection method comprising: bringing the Raman-active particles according to claim 1 into contact with an analyte and irradiating excitation light thereon.

9. The Raman-active particle of claim 1, wherein the plasmonic metal shell comprises one or more metals selected from gold, silver, platinum, palladium, nickel, aluminum, and copper.

10. The Raman-active particle of claim 1, wherein each of the plasmonic metal core and the plasmonic metal shell comprises one or more metals selected from gold, silver, platinum, palladium, nickel, aluminum, and copper.

11. A method of producing Raman-active particles, the method comprising:
a) forming a self-assembled monolayer including a Raman reporter on a spherical plasmonic metal core; and
b) using a reaction solution in which a buffer solution, the metal core on which the self-assembled monolayer is formed, and a plasmonic metal precursor are mixed, to form a plasmonic metal shell which surrounds the metal core on which the self-assembled monolayer is formed and has surface unevenness,
wherein each of said plasmonic metal core and said plasmonic metal shell is a metal that generates surface plasmon by interaction with light,
wherein said plasmonic metal shell includes plasmonic metal fine particles,
wherein the surface unevenness is generated from the plasmonic metal fine particles having an average size of 0.1 D to 0.6 D, based on a diameter (D) of the metal core,
wherein the Raman reporter includes a Raman-active molecule,
wherein the Raman-active molecule is 1,4-benzenedithiol (BDT), and
wherein a standard deviation of a Raman signal intensity is 8.0 or less.

12. The method of producing Raman-active particles of claim 11, wherein a plasmonic metal in the plasmonic metal precursor is one or two or more selected from gold, silver, platinum, palladium, nickel, aluminum, and copper.

13. The method of producing Raman-active particles of claim 11, wherein a mole ratio obtained by dividing the number of moles of a buffer of the buffer solution by the number of moles of the plasmonic metal precursor is 10 to 100.

14. The method of producing Raman-active particles of claim 11, wherein a molar concentration of the buffer of the buffer solution is 10 to 200 mM.

15. The method of producing Raman-active particles of claim 11, wherein the buffer solution includes one or more selected from 4-(2-hydroxyethyl)-1-piperazineethanesulfonic acid (HEPES), 4-(2-hydroxyethyl) piperazine-1-ethanesulfonic acid (MES), phosphated buffered saline (PBS), tris(2-amino-2-hydroxymethylpropne-1,3-idol), phosphate buffer (PB), 3-(N-morpholino) propanesulfonic acid (MOPS), 3-[[1,3-dihydroxy-2-(hydroxymethyl) propan-2-yl]amino]propane-1-sulfonic acid (TAPS), and piperazine-N,N'-bis(2-ethanesulfonic acid) (PIPES).

16. The method of producing Raman-active particles of claim 11, wherein the metal core has a diameter of 20 to 100 nm.

17. The method of producing Raman-active particles of claim 11, further comprising: c) fixing a receptor bonded to an analyte to the metal shell, after b).

* * * * *